(12) United States Patent
Koubeissi

(10) Patent No.: US 9,669,214 B2
(45) Date of Patent: Jun. 6, 2017

(54) ELECTRICAL STIMULATION OF THE CLAUSTRUM/PIRIFORM CORTEX FOR TREATMENT OF EPILEPSY

(71) Applicant: The George Washington University, Washington, DC (US)

(72) Inventor: Mohamad Z. Koubeissi, Washington, DC (US)

(73) Assignee: The George Washington University, Washington, DC (US)

( * ) Notice: Subject to any disclaimer, the term of this patent is extended or adjusted under 35 U.S.C. 154(b) by 0 days.

(21) Appl. No.: 15/080,732

(22) Filed: Mar. 25, 2016

(65) Prior Publication Data

US 2016/0206880 A1 Jul. 21, 2016

Related U.S. Application Data

(63) Continuation of application No. PCT/US2014/057828, filed on Sep. 26, 2014.

(60) Provisional application No. 62/312,219, filed on Mar. 23, 2016, provisional application No. 61/883,744, filed on Sep. 27, 2013.

(51) Int. Cl.
*A61N 1/36* (2006.01)
*A61N 1/05* (2006.01)
*A61B 5/00* (2006.01)
*A61B 5/04* (2006.01)

(52) U.S. Cl.
CPC ...... *A61N 1/36064* (2013.01); *A61B 5/04012* (2013.01); *A61B 5/4094* (2013.01); *A61B 5/4836* (2013.01); *A61N 1/36135* (2013.01); *A61B 5/04001* (2013.01); *A61B 5/7203* (2013.01); *A61B 5/726* (2013.01); *A61B 5/7257* (2013.01); *A61N 1/0534* (2013.01)

(58) Field of Classification Search
None
See application file for complete search history.

(56) References Cited

U.S. PATENT DOCUMENTS 6,793,670 B2 * 9/2004 Osorio ............... A61F 7/12
607/113
7,555,344 B2 * 6/2009 Maschino ......... A61M 5/14276
607/18

(Continued)

FOREIGN PATENT DOCUMENTS

WO WO-2011133583 A1 10/2011

OTHER PUBLICATIONS

International Search Report issued in PCT/US2014/057828 date Jan. 2015, 1 page.

(Continued)

*Primary Examiner* — Brian T Gedeon
(74) *Attorney, Agent, or Firm* — Blank Rome LLP

(57) ABSTRACT

An electrical stimulation device provides stimulation of a person's claustrum and piriform cortex to treat seizures for persons having epilepsy, and to improve consciousness in individuals with disorders of consciousness such as coma. The stimulation device includes a stimulator that generates a stimulation signal, and one or more electrodes located near the target brain regions (Claustrum/piriform cortex). The electrode receives the stimulation signal from said stimulator and imparts the stimulation signal to the target brain regions.

22 Claims, 5 Drawing Sheets

(56) References Cited

U.S. PATENT DOCUMENTS

| | | | | |
|---|---|---|---|---|
| 8,335,664 | B2* | 12/2012 | Eberle | A61B 5/04017 435/287.1 |
| 2007/0027498 | A1 | 2/2007 | Maschino et al. | |
| 2008/0288018 | A1 | 11/2008 | Rezai et al. | |
| 2009/0234419 | A1 | 9/2009 | Maschino et al. | |
| 2009/0248099 | A1 | 10/2009 | Assaf et al. | |

OTHER PUBLICATIONS

International Preliminary Report on Patentability for PCT/US2014/057828 dated Mar. 29, 2016, 1 page.

Written Opinion for PCT/US2014/057828 dated Jan. 6, 2015, 6 pages.

Tononi et al. "The Neural Correlates of Consciousness an Update" Dept. of Psychiarty, Univ. of Wisconisn; Div. of Biology and the Div. of Engineering and Appl. Science, Pasadena, CA; Ann. N.Y. Acad. Sci. 1124:239-261 (2008).

Demertzi et al., Consciousness Supporting Networks; Current Opinion in Neurobiology 2013, 23:239-244.

Blumenfeld "Epilepsy and the Consciousness System: Transient Vegetative State?" Nuerol Clin 29 (2011) 801-823.

Arthuis et al. "Imparied consciousness during temporal seizures is related to increased long-distance cortical-subcortical synchronization" BRAIN, A Journal of Neurology, 2009: 132; 2091-2101.

Bartolomei, et al. "The global workspace (GW) theory of consciousness and epilepsy", Behavioural Neurology 24 (2011) 67-74.

Blumenfeld "Imparied consciousness in epilepsy", The Lancet/Neurology vol. 11 Sep. 2012; pp. 814-826.

F. Bartolomei, et al. "Pre-ictal synchronicity in limbic networks of mesial temporal lobe epilepsy" Epilepsy Research 61 (2004) 89-104.

Selimbyoglu et al. "Electrical stimulation of the human brain: perceptual and behavioral phenomena reported in the old and new literature", Human Neuroscience May 2010; vol. 4, Article 46, pp. 1-11.

Isnard et al. Clinical Manifestations of Insular Lobe Seizures: A Stereo-electroencephalographic Study; Epilepsia, 45(9): 1079-1090, 2004.

Penfield, "Some Mechanisms of Consciousness Discovered During Electrical Stimulation of the Brain" National Academy of Sciences, vol. 44. No. 2, Feb. 15, 1958. pp. 51-66.

Kurth et al. "A link between the systems: functional differentiation and integration within the human insula revealed by meta-analysis" Brain Struct Funct. (2010) 214:519-534.

Crick et al. "What is the function of the claustrum?" Phil. Trans. R. Soc. B (2005) 360, 1271-1279.

Lambert, et al. "Alteration of global workspace during loss of consciousness:A study of parietal seizures" Epilepsia, 53(12):2104-2110, (2012).

Gabor et al. "Alterations of Behavior Following Stimulation of the Claustrum of the Cat", Electroenceph. clin. Neurophysiol., 1964, 17:513-519 Following Stimulation of the Claustrum of the Cat.

Laufs, et al. "Converging PET and fMRI evidence for a common area involved in human focal epilepsies" Neurology: Aug. 2011, pp. 904-910.

Witter et al. "Reciprocal Connections of the Insular and Piriform Claustrum with Limbic Cortex: An Antaomical Study in the Cat" Neuroscience Vo. 24, No. 2, pp. 519-539, 1988.

* cited by examiner

ELECTRICAL STIMULATION OF THE CLAUSTRUM/PIRIFORM CORTEX FOR TREATMENT OF EPILEPSY

RELATED APPLICATIONS

This application is a continuation of PCT/US2014/057828, filed Sep. 26, 2014, which claims the benefit of U.S. Provisional Application No. 61/883,744, filed Sep. 27, 2013. This application also claims priority to U.S. Provisional Application No. 62/312,219, filed Mar. 23, 2016. The entire contents of those applications are incorporated herein by reference.

FIELD OF THE INVENTION

The present invention relates to the use of electrical stimulation to treat illness, and more particularly to the electrical stimulation of the brain to treat epilepsy.

BACKGROUND OF THE INVENTION

Epilepsy affects 1% of the population. Two thirds of individuals with epilepsy will respond to antiepileptic medications and the remaining third are medically intractable, i.e. do not respond to antiepileptic medications. In the United States, 3 million people have epilepsy making the intractable population close to 1 million individuals. Existing technology has resulted in very limited benefits in terms of controlling seizures in patients with intractable partial or generalized epilepsy.

Although the neural mechanisms that underlie consciousness are unclear, clinicians tend to separate it into wakefulness and awareness. Wakefulness depends upon the functional integrity of subcortical arousal systems in the brainstem and thalamus [1]. Awareness refers to the content of experience as regards both the environment and the self, and is thus defined as the capacity to respond to external stimuli while having an internal and qualitative experience of existence. The external awareness network seems to encompass bilateral dorsolateral prefrontal cortices and lateral posterior parietal cortices, whereas the internal awareness network seems to include midline posterior cingulate cortex/precuneus and anterior cingulate/medial prefrontal cortices [2]. A complete disruption of consciousness during the waking state, involving the perception of both external and internal stimuli, is experienced in many medical conditions that affect the brain primarily or secondarily including, though not limited to, coma and epilepsy, regardless of the area of seizure origin in the brain. Indeed, disruption of consciousness is one of the most disabling manifestations of epileptic seizures that affects the quality of life [3]. However, the precise structures and pathophysiological mechanisms involved in impairment of consciousness in epileptic seizures remain a matter of debate [4-6].

Common brain regions are thought to be involved in all seizures that interfere with consciousness, regardless of their onset zones and variations in semiology. These regions include the fronto-parietal association cortex and the subcortical arousal system in the brainstem and thalamus [6]. One hypothesis suggests that alteration of consciousness in partial seizures results from abnormal synchronization of cortical activity between distant brain regions [4] that overloads the structures involved in consciousness processing, affecting their ability to handle incoming information [5, 7].

As discussed in WO2014/113578, which is hereby incorporated by reference, temporal lobe epilepsy is the most common focal epilepsy in adolescents and adults, and the most frequent indication for epilepsy surgery. Mesial temporal lobe epilepsy (MTLE) often originates from the hippocampus, which is implicated in declarative memory function. A clinical trial in patients with intractable MTLE showed that temporal lobectomy is superior to continued medical therapy in achieving seizure freedom. However, resection is generally eschewed if pre-surgical evaluation predicts functional deficits. Additionally, more than half of all intractable patients are not candidates for surgical resection. The risk of memory decline after hippocampal resection depends on the structural integrity of the hippocampus and its degree of contribution to memory function prior to surgery. A non-lesional, language dominant hippocampus and good preoperative memory function often exclude MTLE patients from temporal lobectomy because of the high-risk of postoperative memory decline. This underlies the need to pursue controlling disabling hippocampal seizures without compromising memory function.

While surgical resection of the temporal lobe is an effective treatment for medically-intractable temporal lobe epilepsy, surgical resection often results in memory impairment. Thus, other approaches including deep brain stimulation (DBS) have been undertaken. Additionally, seizures may original from some brain regions that subserve important functions (e.g., movement or speech, etc.) and thus the patient is not a candidate for surgical resection. DBS in epilepsy has targeted gray matter structures using high frequencies, but has not achieved desired results. Conventional DBS may provide a first stimulation when there is no prediction of an impending seizure but may provide a second altered stimulation based on a prediction of an impending seizure, where the prediction is based on monitoring naturally occurring, organically generated signals. For example, conventional systems may be programmed to detect and record seizure activity based on signals generated naturally in the brain by the brain itself. Conventional systems may also be configured to control stimulation as a function of the detected or recorded seizure activity.

DBS has risen as an effective treatment in patients with movement or psychiatric disorders. The stimulation targets specific areas in the brain, altering the function of circuits or inducing neurogenesis and other plastic changes. DBS has been approved for treatment of Parkinson's disease, essential tremor, dystonia, and obsessive-compulsive disorder, but its success in epilepsy has been limited. Most stimulation trials in epilepsy have used high frequencies.

The claustrum is a telencephalic subcortical structure. It is a thin sheet of grey matter underneath the insula, which is part of the neocortex. The claustrum is a curved sheet that is oriented sagittally between the white matter tracts of the external capsule and extreme capsule. It is lateral to the putamen and medial to the insular cortex and is considered by some sources to be part of the basal ganglia. There are lateral and medial tracts connecting the claustrum to many parts of the cortex and perhaps to the hippocampus, the amygdala, and the caudate nucleus (connections with subcortical centers are a matter of debate). One claustrum is present on each side of the brain. Although the exact function of the claustrum remains to be verified, connectivity studies have shown that the claustrum plays a strong role in communication between the two hemispheres of the brain, specifically between cortical regions controlling attention. See Wikipedia, Claustrum.

The piriform cortex situated caudally to a dorsal area, which is caudal to a hippocampal area. The piriform cortex contains a critical, functionally defined epileptogenic trigger zone, "Area Tempestas". From this site in the piriform cortex chemical and electrically evoked seizures can be triggered. It is the site of action for the proconvulsant action of chemoconvulsants. See Wikipedia, Piriform Cortex.

SUMMARY OF THE INVENTION

The present invention provides significant seizure control in persons having epilepsy. Another potential use is in patients with disorders of consciousness, such as coma, in order to stimulate consciousness. An electrical stimulation device is provided for stimulation of a person's target brain regions TBR (i.e., the claustrum/piriform cortex) to treat seizures for persons having epilepsy, or to treat coma. The stimulation device includes a stimulator that generates a stimulation signal, and one or more electrodes located near the TBR (i.e., the claustrum/piriform cortex). The electrode receives the stimulation signal from said stimulator and imparts the stimulation signal to the TBR (i.e., the claustrum/piriform cortex).

DETAILED DESCRIPTION OF THE PREFERRED EMBODIMENTS

Figure 1:
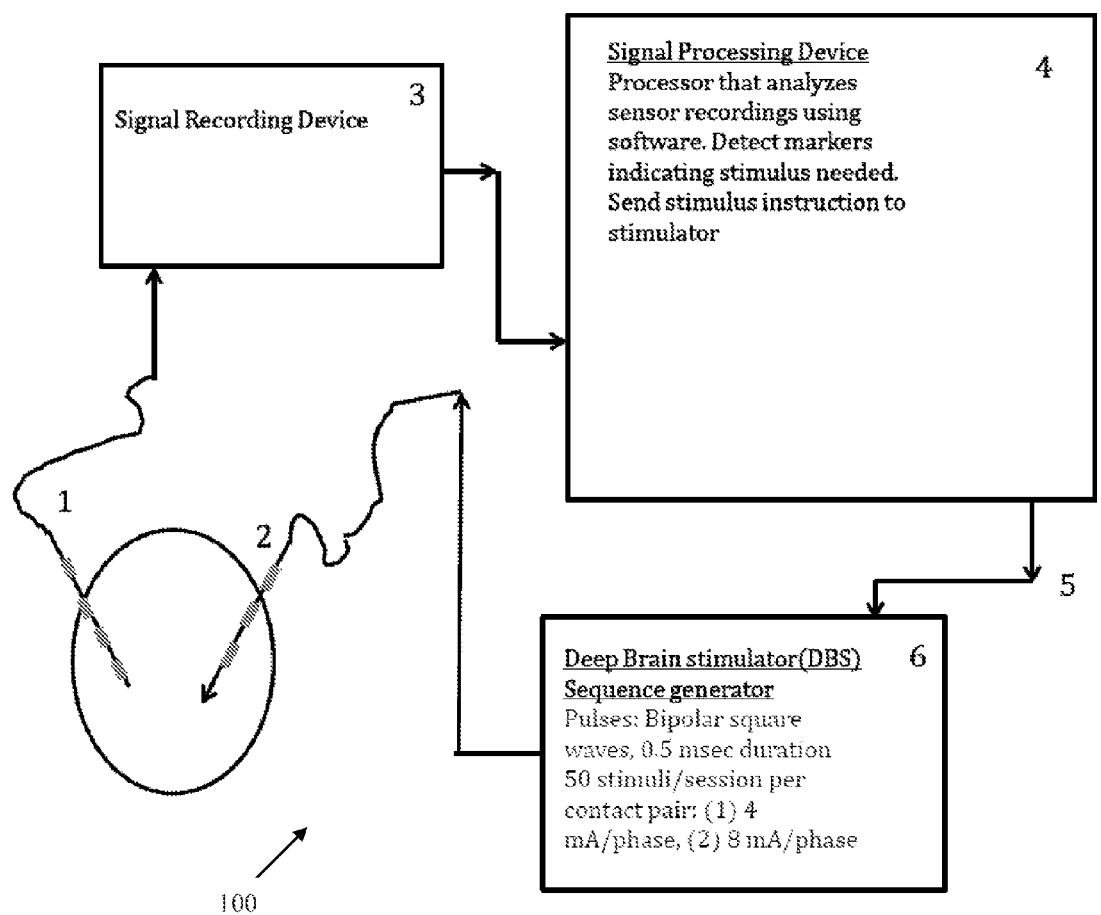
FIG. 1 is a block diagram showing the stimulation system for electrical stimulation of the TBR (i.e., the claustrum/piriform cortex) to treat epilepsy.

In describing the preferred embodiments of the present invention illustrated in the drawings, specific terminology is resorted to for the sake of clarity. However, the present invention is not intended to be limited to the specific terms so selected, and it is to be understood that each specific term includes all technical equivalents that operate in a similar manner to accomplish a similar purpose.

Referring to the drawings, FIG. 1 shows a non-limiting illustrative embodiment of the electrical stimulation system 100 in accordance with the invention. The system 100 includes first and second electrodes 1, 2, a signal recording device 3, a signal processing device 4, and a deep brain stimulator (DBS) 6. As shown, the first electrode 1 is connected to and in electrical communication with the signal recording device 3, and the second electrode 2 is connected to and in electrical communication with the DBS 6. The signal processing device 4 is connected to and in electrical communication with both the signal recording device 3 and the DBS 6. Though the connections are shown to be by wire, the signals between the signal recording device 3, the DBS 6 and the signal processing device 4 can be communicated wirelessly.

The first electrode 1 is placed in the seizure onset zone (call it Es), regardless of where that is in the brain. The second electrode 2 (call it Ec) is placed in the target brain regions TBR (i.e., the claustrum/piriform cortex) to impart a stimulation to the patient. The first electrode 1 detects the seizure discharges and transmits them to signal recording device 3. The first electrode 1 is positioned to detect seizure discharges, and can be implanted in the patient's seizure focus area, which can be determined by noninvasive and invasive monitoring as per routine care of individuals with intractable epilepsy. The signal recording device 3 records the signals, including any seizure discharges, and passes the signal to the signal processing device 4. The signal recording device 3 records the signal and stores it for later download and analysis in order to refine seizure detection and make it more accurate, i.e. with less false positives and less false negatives.

The signal processing device 4 analyzes the received signal and determines if the patient is having a seizure. The signal processing device 4 software can determine if the received signal is a seizure discharge in accordance with known suitable techniques, such as discussed in *Automatic seizure detection in long-term scalp EEG using an adaptive thresholding technique: a validation study for clinical routine*, Hopfengärtner R, Kasper B S, Graf W, Gollwitzer S, Kreiselmeyer G, Stefan H, Hamer H. Clin Neurophysiol. 2014 July; 125(7):1346-52. doi: 10.1016/j.clinph.2013.12.104. Epub 2014 Jan. 7.PMID: 24462506, the entire contents of which are hereby incorporated by reference. One main criteria of a seizure discharge is the regularity of rhythmic runs of sharply contoured waveforms, and importantly the gamma power as determined by time—frequency decomposition and analysis. For instance, the signal processing device 4 can analyze the amplitude, frequency, frequency content, shape, time, duration, wave form, pulse width, current amplitude, voltage amplitude or other properties of the signals that are detected by the first electrode 1. Seizure detection paradigms used in the signal processing device 4 to analyze the signal and detect seizures include, among possible others, spike frequency, spike amplitude, and power analysis. The latter may be done through wavelet analysis, fast Fourier transform, matching pursuit method, Gabor transform method, or any other appropriate analysis that will generate time frequency decomposition of the signal and calculate the power. The signal processing device 4 can detect markers that indicate that a seizure is taking place or that stimulation is otherwise needed. The signal processing device 4 is flexible enough to be able to teach it a particular patient's seizure pattern based on which it should deliver the stimulation pulses.

If the signal processing device 4 determines that the patient is having a seizure, the signal processing device 4 transmits a command signal 5 to the DBS 6. Thus, the signal processing device 4 controls the operation of the DBS 6. For instance, the command signal can be an ON/OFF control signal 5 that operates to turn the DBS 6 ON or OFF. In the default state, the DBS 6 is OFF, and the signal processing device 4 transmits an ON signal 5 to turn ON the DBS 6. In the OFF state, the DBS 6 does not send any signal over the second electrode 2. However, when the DBS 6 receives an appropriate command signal 5 from the signal processing device 4, it generates a stimulation signal that it transmits to the second electrode 2. The DBS 6 can be for instance, a signal generator that generates a signal with a desired signal characteristics such as frequency, amplitude, wave form, pulse width, current amplitude, voltage amplitude, and other properties, and can produce certain wave forms (such as sinusoidal or square wave forma) that can be predefined and set for the DBS 6 or can be controlled by the signal processing device 4 and specified in the command signal.

The second electrode 2 delivers that stimulation signal to the patient's TBR (claustrum/piriform cortex). The stimulation signal can be a monopolar, bipolar, or sinusoidal signal with 0.01 to 5 msec duration, at frequencies ranging from 0.01-250 Hz, current intensity of 0.1 mA to 20 mA and for durations of 5 msec to infinity. The first electrode 1 can continue to detect signals as the stimulation signal is being applied. However, the stimulation is expected to stop the seizure discharge, so that the signals the seizure detection and analysis will continue to read the seizure discharge and activates further electrical stimulation this until seizure discharge abates. Accordingly, the stimulation signal can be applied for a predetermined period of time. Or, the stimulation signal can continue to be applied until the signal processing device 4 determines that the signals detected from the first electrode 1 no longer detects a seizure discharge, or until a maximum predetermined period of time has elapsed.

The entire cycle works substantially in real time without any imposed delays. Thus, the patient's brain signals are detected by the first electrode 1 and send to the signal recording device 3 in real time. The signal recording device 3 transmits those received signals to the signal processing device 4 in real time, the signal processing device 4 analyzes those received signals in real time and generates a command signal 5 in real time. And, the DBS 6 generates and imparts a stimulation signal to the patient's brain in real time upon receipt of the command signal 5. The entire process is conducted automatically and without any manual interaction, so that it can occur substantially in real time without any delays.

In addition, while the signal recording device 3, signal processing device 4, and DBS 6 are shown as separate devices, it should be recognized that they can all be integrated in a single device having a single housing. In addition, it should be appreciated that the signal recording device 3 need not be provided if recording is not used, or the signal recording can be performed by the signal processing device 4. Still further, it is noted that the embodiment of FIG. 1 shows the electrodes 1, 2 extending from inside the patient's brain to outside the patient's brain, and that the signal recording device 3, signal processing device 4 and DBS 6 are all located outside the patient. It should be readily apparent that the entire system 100 can be made portable and permanently worn by the patient. For instance, the signal recording device 3, signal processing device 4 and DBS 6 can be provided in a single housing that is carried by the patient or implanted into the patient. And the electrodes 1, 2 need not extend outside the patient, but can be fully implanted.

FIG. 1 shows the deep brain electrode sensor 1 in position in a patient-specific seizure onset zone or near the TBR (i.e., the claustrum/piriform cortex). Though a single electrode 1 is shown, more than one electrode can be utilized. If a patient has more than one seizure focus, a different electrode can be placed in each seizure focus for detection of seizure onset and delivery of electrical stimulation. The second deep brain electrode 2 is positioned near the TBR (i.e., the claustrum/piriform cortex). Though a single electrode 2 is shown, more than one electrode can be utilized. That second electrode(s) 2 can be located near the anterior, posterior, dorsal, or ventral claustrum in addition to anterior, posterior, dorsal, or ventral piriform cortex. It can also be located on left or right side. However, the electrodes 1, 2 are preferably within the TBR (i.e., the claustrum/piriform cortex) or within 2 mm from the TBR (i.e., the claustrum/piriform cortex) so that the first electrode 1 can detect any seizure discharges and the second electrode 2 can impart the stimulation signal directly to the TBR (i.e., the claustrum/piriform cortex).

It is noted that FIG. 1 shows that the first electrode 1 is used to sense brain activity and the second electrode 2 is used to impart a stimulation signal to the patient. However, the deep brain electrodes 1 and/or 2 can have dual functions of sensing electrical activity of the brain and delivering the stimulation sequence to the brain. Deep brain electrodes 1, 2 that perform dual functions are located near the TBR (i.e., the claustrum/piriform cortex). The deep brain electrode sensors 1 that do not perform dual functions may be located at a seizure onset zone that is not near the TBR (i.e., the claustrum/piriform cortex).

Figure 2A:
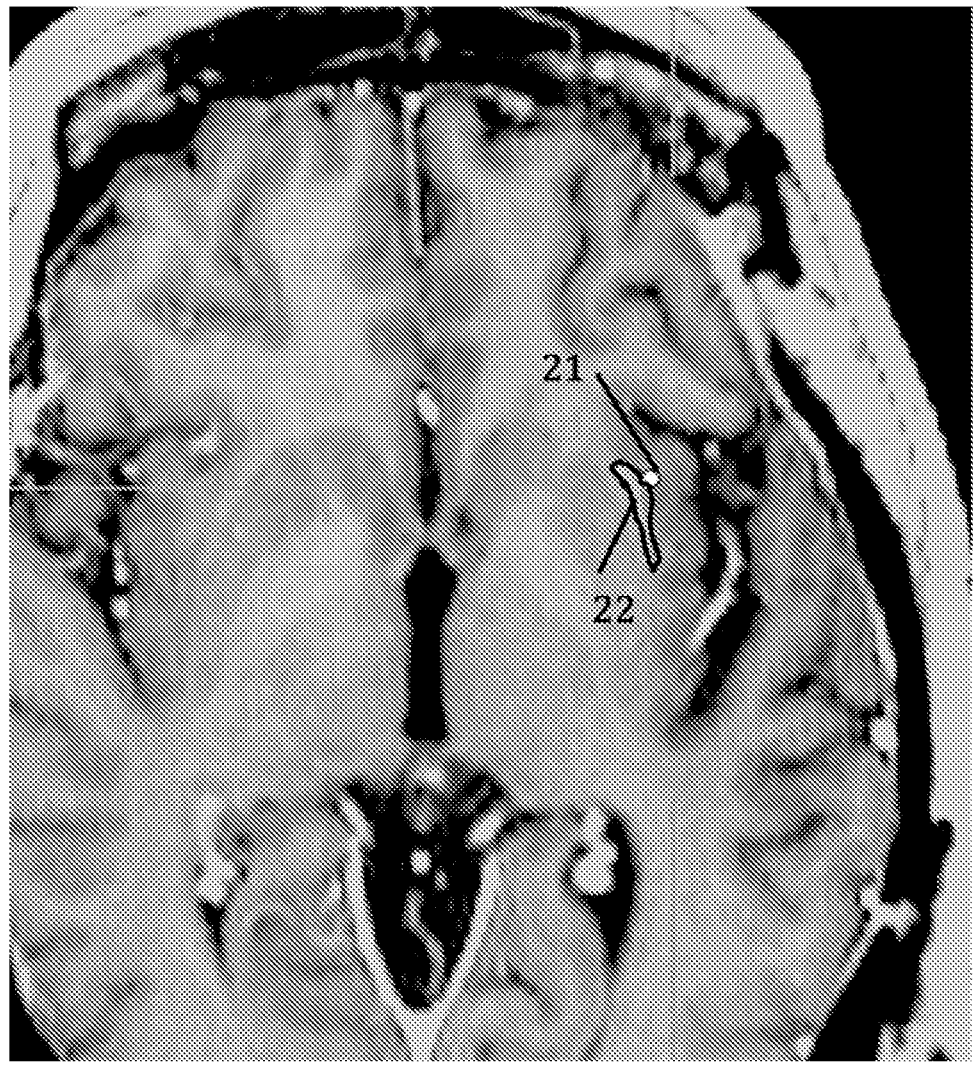
FIGS. 2A-2C are cross-section illustrations of a brain having electrodes placed in the TBR (i.e., the claustrum/piriform cortex) of a patient.
Figure 2B:
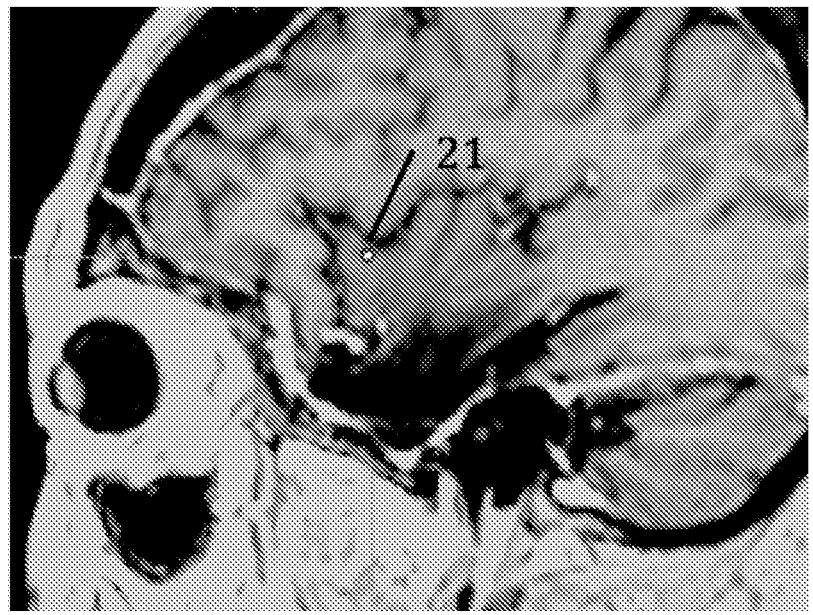
Figure 2C:
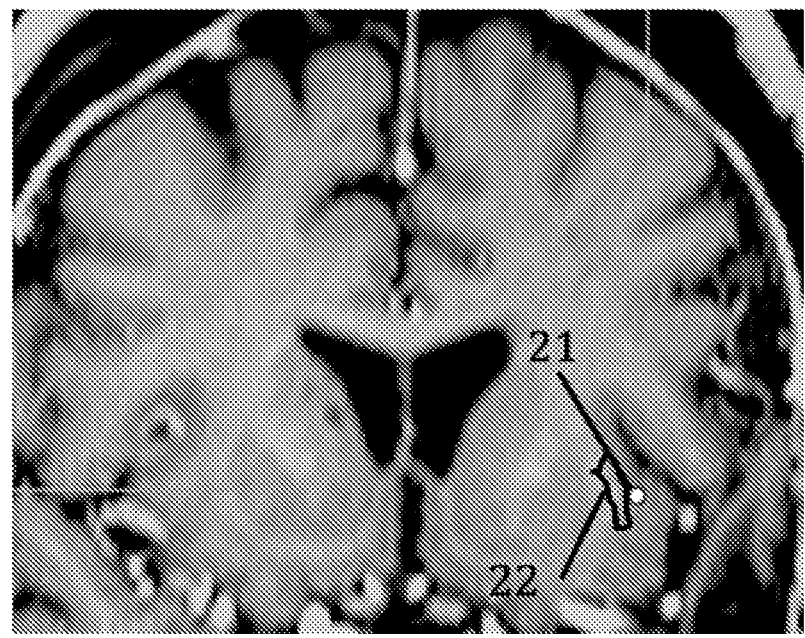

FIGS. 2A-2C show the location of an electrode 21 (the second electrode 2) whose stimulation elicited impairment of consciousness. The location is shown in three different planes, and was determined by superimposition of pre-operative brain Mill with post-operative volumetric CT scan according to anatomic fluids. The region inside the solid black line 22 is the claustrum. Accordingly, the electrode 21 abuts (i.e., directly touches) the patient's claustrum.

Figure 3:
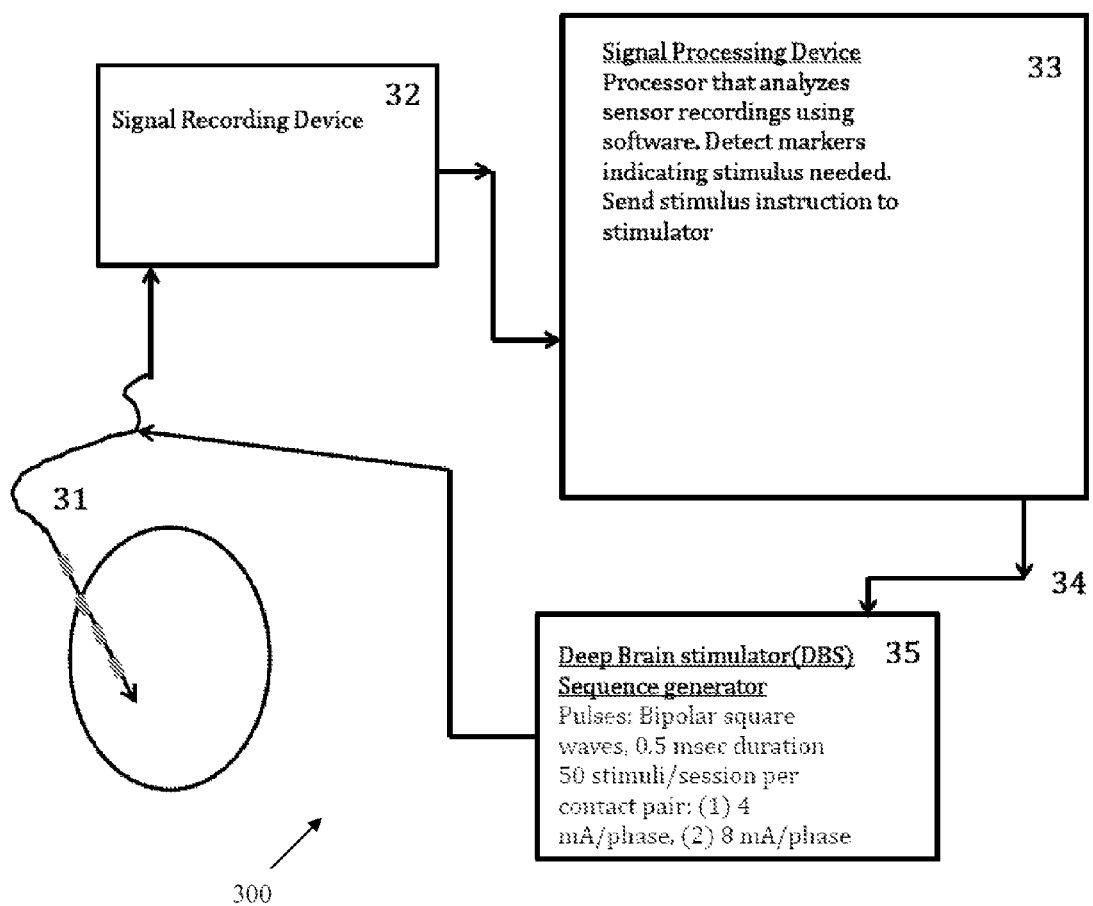
FIG. 3 is a block diagram of a stimulation system having a single electrode.

FIG. 3 shows a system 300 having a deep brain electrode 31 positioned near the patient's TBR (i.e., the claustrum/piriform cortex). The electrode 31 is used to provide stimulation, and can also be used as a sensor. Though one electrode 31 is shown, more than one electrode can be provided. The electrode 31 can be located near anterior, posterior, dorsal, or ventral claustrum in addition to anterior, posterior, dorsal, or ventral piriform cortex. The electrode 31 can also be located on the left or right side. The electrode 31 can operate the same as the first and/or second electrodes 1, 2 of FIG. 1. And the signal recording device 32, signal processing device 33, command signal 34 and DBS 35 operate the same as the respective elements of FIG. 1. Here, the signal recording device 32 receives sensed signals from the electrode 31, and the DBS 35 imparts the stimulation signal to that same electrode 31.

Figure 4:
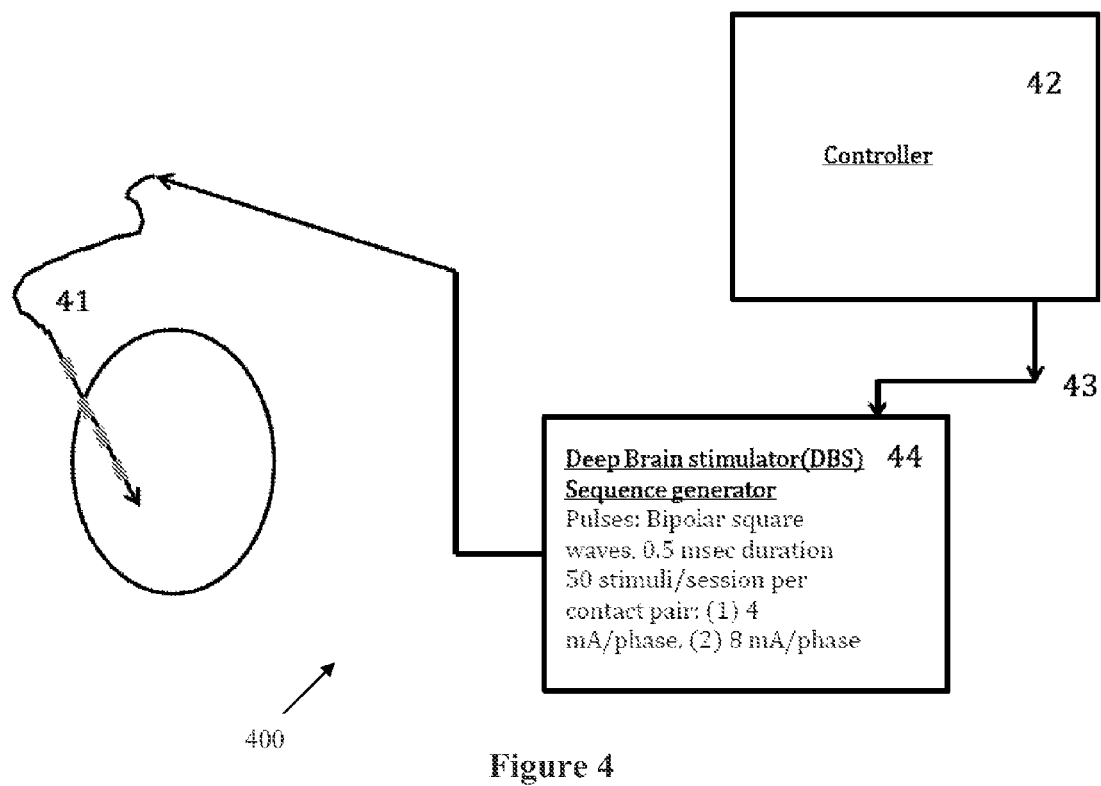
FIG. 4 is a block diagram of a stimulation system having a deep brain stimulator (DBS).

FIG. 4 is another embodiment of the system 400 of the present invention. Here, a deep brain electrode 41 is provided near the patient's TBR (i.e., the claustrum/piriform cortex) to provide stimulation. Though one electrode 41 is shown, more than one electrode can be utilized. The electrode 41 can be located near anterior, posterior, dorsal, or ventral claustrum in addition to anterior, posterior, dorsal, or ventral piriform cortex. It can be located on left or right side. A controller 42 is provided to activate or deactivate sequence generator. The controller 42 sends an ON/OFF control command signal to the DBS 44. The DBS 44 generates a deep brain stimulation sequence and sends it to the implanted deep brain sensing electrode(s) to stimulate brain.

Thus, FIG. 4 shows the system 400 without the recording device 3 of FIG. 1, and with a controller 42 instead of a single processing device 4, and having a single electrode 41. The electrode 41 is only provided to impart a stimulation signal to the patient. Thus, the electrode 41 does not sense brain activity, and the controller 42 does not analyze brain activity or determine if the patient is having a seizure. Instead, the controller 42 can be utilized by a user to manually control the DBS 44 to impart a stimulation signal to the patient through the electrode 41. The user utilizes the controller 42 to impart a control signal 43 to the DBS 44 to generate a stimulation signal. This can be done, for instance, by having a control button or the like on the controller 42. Or the controller 42 can receive a wireless signal from a remotely located controller that is operated by a third person. The electrode 41, controller 42, command signal 43 and DBS 44 can be implemented in the same way as those respective elements of FIGS. 1-3.

The present invention of FIGS. 1-4 is related to the therapeutic effects of electrical stimulation of the claustrum in patients with pharmacoresistant epilepsy. The claustrum may be the brain structure that is involved in alteration of awareness that accompanies seizures. This invention covers two modes of electrical stimulation: scheduled and closed loop (i.e., responsive neurostimulation). The latter means that a seizure detection device may be inserted in or around the seizure onset zone which will trigger the stimulator and inhibit loss of consciousness or alteration of awareness that may be related to propagation of the seizure discharge to the TBR (i.e., the claustrum/piriform cortex). One use would be a scheduled stimulation: i.e. the pulse generator will deliver electrical stimulation regardless of seizure occurrence. An example could be low frequency stimulation at 1 or 5 Hz, 4 hours on and 4 hours off around the clock. Another use would be delivery of stimulation only upon detection of seizure activity. The electrodes can be implanted in (or within 2 mm of) the ventral and dorsal TBR (i.e., the claustrum/piriform cortex), on the right and left sides, and provide stimulation with very low frequencies ranging to very high frequencies. In one embodiment, frequencies can be in the range of 0.01 Hz to 250 Hz.

The main target population to benefit from this intellectual property will be individuals with pharmacoresistant epilepsy. However other patients can benefit as well, such as persons with certain psychiatric and cognitive disorders, including, but not limited to ones with attention deficit, autism, Asperger's, and schizophrenia.

This technology can be implemented as a stimulator, either isolated or part of a closed loop system, and identification of ideal stimulation parameters to minimize seizures in patients with epilepsy, and control cognitive and psychiatric symptoms in individuals with such problems.

The present invention has a number of advantages, including: the target location of deep brain stimulation TBR (i.e., the claustrum/piriform cortex) the stimulation parameters which are likely to be low frequency (of note, most, if not all DBS trials done for epilepsy have used high frequency stimulation), and the potential use of either an open (scheduled with predefined duty cycle) or a closed loop system (i.e., delivery of electrical stimulation only at the time of a seizure instead of around the clock).

In the embodiments of FIGS. 1-4, the signal processing device 4, 33 (as well as the signal recording device 3, 32, and/or the DBS 6, 35, 44, and/or the controller 42) can include a processing device to perform various functions and operations in accordance with the invention. The processing device can be, for instance, a computer, personal computer (PC), server or mainframe computer, or more generally a computing device, processor, application specific integrated circuits (ASIC), or controller. The processing device can be provided with one or more of a wide variety of components or subsystems including, for example, a co-processor, register, data processing devices and subsystems, wired or wireless communication links, input devices (such as touch screen, keyboard, mouse) for user control or input, monitors for displaying information to the user, and/or storage device(s) such as memory, RAM, ROM, DVD, CD-ROM, analog or digital memory, flash drive, database, computer-readable media, floppy drives/disks, and/or hard drive/disks. All or parts of the system, processes, and/or data utilized in the invention can be stored on or read from the storage device(s). The storage device(s) can have stored thereon machine executable instructions for performing the processes of the invention. The processing device can execute software that can be stored on the storage device.

The processing device can also be connected to the Internet, such as by a wireless card or Ethernet card. The processing device can interact with a website to execute the operation of the invention, such as to present output, reports and other information to a user via a user display, solicit user feedback via a user input device, and/or receive input from a user via the user input device. For instance, the processing device can be part of a mobile smart phone running an application (such as a browser or customized application) that is executed by the processing device and communicates with the user and/or third parties via the Internet via a wired or wireless communication path.

The present invention is based on the findings discussed in the example below. The example is provided to illustrate the invention, without intending to limit the scope of the invention. The example is findings that illustrate the role of the brain region (TBR (i.e., the claustrum/piriform cortex) in consciousness suggesting that prolonged stimulation (likely with low frequencies at low current intensities) can induce changes in the brain that lead to better seizure control potentially in both focal and generalized epilepsies.

Illustrative Example

A finding from the electrical stimulation of the brain during presurgical evaluation of intractable epilepsy in a patient provided direct evidence that a small brain region that encompasses the anterior-dorsal insula and the neighboring TBR (i.e., the claustrum/piriform cortex) (FIG. 2) is a key component of the network supporting both external and internal awareness. No similar response to electrical stimulation of any other brain region has ever been reported, despite almost a century of experience in electrical cortical stimulation [8].

A region in the human brain where electrical stimulation reproducibly disrupted consciousness is described. A 54 year-old woman with intractable epilepsy underwent depth electrode implantation and electrical stimulation mapping. The electrode whose stimulation disrupted consciousness was between the left TBR (i.e., the claustrum/piriform cortex) and anterior-dorsal insula. Stimulation of electrodes within 5 mm did not affect consciousness. We studied the interdependencies amongst depth recording signals as a function of time by nonlinear regression analysis (h2 coefficient) during stimulations that altered consciousness and stimulations of the same electrode at lower current intensities that were asymptomatic. Stimulation of the claustral electrode reproducibly resulted in a complete arrest of volitional behavior, unresponsiveness, and amnesia without negative motor symptoms or mere aphasia. The disruption of consciousness did not outlast the stimulation, and occurred without any epileptiform discharges. We found a significant increase in correlation for interactions affecting medial parietal and posterior frontal channels during stimulations that disrupted consciousness compared with those that did not. Our findings suggest that the left TBR (i.e., the claustrum/piriform cortex)/anterior insula is an important part of a network that subserves consciousness and that disruption of consciousness is related to increased EEG signal synchrony within frontal-parietal networks.

In more detail, the 54 year-old woman with a history of intractable epilepsy, characterized by olfactory auras followed by disruption of consciousness and occasional secondarily generalized seizures, underwent left hippocampectomy sparing the amygdala. The patient remained seizure-free for four years before habitual seizures recurred necessitating depth electrode evaluation. Since the seizures were consistent with mesial temporal origin, intraparenchymal electrodes were implanted in the anterior hippocampal remnant and in structures that have known connectivity with the mesial temporal structures: the left amygdala, posterior cingulate gyms, medial and lateral frontal regions, and anterior and posterior insula, in addition to two electrodes in the posterior quadrant sampling the temporo-parietal and temporo-occipital regions. Bilateral scalp electrodes were also placed. No subdural electrodes were placed. One depth electrode that sampled the left anterior insula included a contact, AI4, in the extreme capsule and in close proximity to the anterior insular cortex and the TBR (i.e., the claustrum/piriform cortex) (FIG. 2).

Cortical Synchrony Assessment

We studied interdependencies between signals from different brain regions by using non-linear regression analysis during stimulations that interfered with consciousness and those that did not. For this, our aim was to assess changes in synchronization between remote brain regions, particularly fronto-parietal networks, during AI4 stimulations that induced disruption of consciousness (14 mA) and compare them with control stimulations of the same electrode at lower current intensities (2-12 mA) that did not interfere with consciousness. Interdependencies between bipolar signals recorded from 15 contacts that sampled evenly most implanted regions, including frontoparietal areas, were estimated as a function of time by using non-linear regression analysis.

Details of the method are described elsewhere [4]. Non-linear regression analysis provides a parameter, referred to as the non-linear correlation coefficient $h^2$, whose values lie in the range [0, 1]. Low values of $h^2$ denote independence of signals, whereas high values of $h^2$ denote signal dependence by signifying that one signal is related via a (likely non-linear) transformation to another. The analysis was performed over a sliding window of two-second duration by steps of 0.25 s. The $h^2$ values were averaged over each period of interest defined below, for each of the 105 considered pairs of signals and for two AI4 stimulations that interfered with consciousness and two control stimulations (at 6 mA) of the same electrode that did not interfere with consciousness.

To assess the functional connectivity between parieto-frontal cortices, we chose 3 bipolar channels from medial parietal cortex, including the precuneus; 4 from lateral frontal region; 5 from anterior frontal region; and 3 from medial frontal region. $h^2$ values were computed on broad-band signals (0.5-90 Hz), providing a global estimation of nonlinear interdependencies. Two periods were considered for analysis: a 10-second background (BG) period chosen just before the start of the stimulation and an 8-second period covering the stimulation period (SP). The $h^2$ values were averaged over BG and SP periods. Changes in $h^2$ values obtained during the SP period relative to the BG period were evaluated by calculating the variation of $h^2$ values in term of Z scores [$Zh2=((\text{mean } h2 \text{ (SP)}-\text{mean } h2 \text{ (BG)})/\text{SD (BG)}$]. These values were then averaged over time in order to get an estimate (mean+/−sd) of the degree of coupling between selected channels. For each selected channel, we calculated the $h^2$ values between all possible pairs. The differences in values obtained from positive (disrupting consciousness) versus negative (asymptomatic) stimulations of AI4 were compared using a Mann Whitney test and corrected for multiple comparison using Bonferroni correction.

The patient's seizures originated from the left amygdala. Electrical stimulation of medial frontal electrodes was done initially, and no symptoms were elicited at currents reaching 18 mA. Then, one of these "clinically silent" electrodes was used as a reference for electrical stimulation of all remaining contacts. Stimulating AI4 using biphasic waves at 14 mA (50 Hz, 0.2 msec pulse width, 3-10 second train duration), but not lower intensities, resulted in immediate impairment of consciousness, in 10 out of 10 times, with arrest of reading, onset of blank staring, unresponsiveness to auditory or visual commands, and slowing of spontaneous respiratory movements. The patient returned to baseline as soon as the stimulation stopped with no recollection of the events during the stimulation period. Occasionally, the induced impairment of consciousness was associated with scanty, perseverative, and incomprehensible verbal output consisting of one or two syllables, with a confused look on the face. No abnormal discharges outlasting the stimulation were seen on depth electrode recordings or scalp electroencephalogram (EEG). Specifically, the raw EEG in frontoparietal regions did not show any deviation from baseline during the stimulation step that elicited disruption of consciousness as well as during those that did not. Stimulation of the adjacent electrode contacts did not elicit the same phenomena.

The symptoms elicited by AI4 stimulation could not be attributed to negative motor phenomena because the patient was able to continue repetitive movements with the tongue and hands during stimulation if initiated before the stimulus train. Such movements would continue decrescendo for up to 4 seconds through stimulation before pausing. Also, the finding could not be attributed to aphasia because of maintained ability to repeat a word if the task is initiated before stimulation. The repetition would continue for approximately 2 seconds during the beginning of stimulation, although with some dysarthria, before pausing completely. The patient was unable to recall any words given to during stimulation. Stimulations repeated on the following day showed consistent findings.

In the study of interdependencies between signals from different brain regions by using non-linear regression analysis during stimulations that resulted or not in disruption of consciousness, we found that changes from BG period were dramatically different during stimulations that resulted in disruption of consciousness when compared with "control" stimulations.

Despite decades of electrocortical stimulation mapping as a routine procedure in patients with epilepsy, the disruption of consciousness has never been precipitated by electrical stimulation of any other site in the human brain, including the hippocampus, amygdala, cingulate cortex, or various areas of the insula and other neocortical regions [8-10]. The immediate impairment of consciousness due to direct stimulation of the left anterior-dorsal insula/claustrum region, without any afterdischarges, suggests that this effect arises from functional interruption of the anterior insula, the claustrum, or both. The anterior-dorsal insula seems to play a role in self-awareness and integrates emotional and cognitive inputs, setting the context for actions [11]. However, there have been no previous reports that stimulations of different parts of the insula result in an alteration of consciousness [9] and AI4 was the closest contact to the claustrum, and the stimulation of neighboring contacts that were within 2.7 mm did not elicit such phenomena. Thus, the claustrum—a region in which the effects of electrical stimulations have never been reported to our knowledge in humans—could be a key component of the network supporting "conscious awareness" during wakefulness. The claustrum could constitute a common gate to the "external" and "internal" awareness networks. This could explain why the electrical stimulation of the claustrum, and the resulting alteration of its normal function, would cause an impairment of consciousness, including an absence of recollection of the external events and of internal/interoceptive experience. This may support previous hypotheses that the claustrum is related to the processes that give rise to integrated conscious percepts [12].

We found that stimulations that caused disruption of consciousness were associated with increased correlations in regions participating in the global workspace of consciousness and could block transiently its functioning [5]. This has been found to be the case in temporal lobe [4] and parietal seizures [13] that cause disruption of consciousness. Excessive synchronization between the thalamus and parietal cortex was associated with disruption of consciousness that accompanies temporal lobe seizures, rather than disruption of temporal lobe function alone [4]. Our finding further suggests that the claustrum appears to be a component of the neural correlates of consciousness mediating increased synchronization between various cortical regions.

Another hypothesis regarding the alteration of consciousness that accompanies seizures, the "network inhibition hypothesis", suggests that propagation of ictal discharges from the mesial temporal structures to the brainstem and diencephalon results in inhibition of the subcortical arousal system, which results in widespread depression of cortical activity [6]. Due to a widespread connectivity with neocortical areas, it is possible that the claustrum participates in the widespread cortical depression.

In one study, electrical stimulation of the claustrum resulted in the alteration of awareness in non-anesthetized cats, causing the cats to crouch and close their eyes, and become unresponsive to external stimulation [14]. Indeed, the claustrum may play a role in computational processes that involve different brain areas, by coordinating distant synchronized activities and controlling voluntary behavior. Such a coordination by the claustrum—likened by Crick and Koch to the conductor of an orchestra [12]—would make it an important part of the neural correlates of consciousness. Interestingly, a recent EEG/fMRI study in patients with different focal epilepsies found a common brain region in all patients that showed increased hemodynamic responses in relation to interictal epileptiform discharges, regardless of the localization of interictal and ictal activity [15]. This region was close to the frontal piriform cortex and its Talairach coordinates suggest that it corresponds to the claustrum. As most of the patients suffered from complex partial seizures, this region could be part of an anatomic circuit acting as critical modulator of seizure propagation and could possibly be responsible for the dyscognitive component of focal seizures.

The electric current that elicited disruption of consciousness in our patient was rather high, 14 mA. Thus, one may entertain the possibility that this current might have resulted in afterdischarges or seizures in brain regions that were not implanted with depth electrodes, without necessarily appearing on the scalp electrodes either. However, the patient's disruption of 10 consciousness immediately reversed upon termination of the stimulation train, which suggests that it was directly induced by stimulation of the insula/claustrum region as it did not outlast the stimulus like afterdischarges or seizure discharges. In addition, though stimulating the left claustrum interferes with only left hemispheric, the present invention can also be utilized to stimulate right hemispheric or bilateral networks.

Thus, loss of consciousness can be artificially induced by electrical stimulation of a specific and limited brain region. This is the first report of a loss of consciousness induced by the stimulation of a limited area of the brain. A therapeutic implication could be deep brain stimulation of the region at lower current intensities or low frequencies in order to treat the disruption of consciousness occurring in epilepsy.

FIG. 2 shows the location of the AI4 contact 21 whose stimulation elicited impairment of consciousness. The location, shown in three different planes, was determined by superimposition of pre-operative brain Mill with post-operative volumetric head CT scan according to anatomic fiducials. The claustrum 22 is highlighted to show its proximity to the stimulating contact.

The references noted below and above are hereby incorporated by reference: (1) Tononi, G. and C. Koch, The neural correlates of consciousness: an update. Ann N Y Acad Sci, 2008. 1124: p. 239-61. (2) Demertzi, A., A. Soddu, and S. Laureys, Consciousness supporting networks. Curr Opin Neurobiol, 2013. 23(2): p. 239-44. (3) Blumenfeld, H., Epilepsy and the consciousness system: transient vegetative state? Neurol Clin, 2011. 29(4): p. 801-23. (4) Arthuis, M., et al., Impaired consciousness during temporal lobe seizures is related to increased long-distance cortical-subcortical synchronization. Brain, 2009. 132(Pt 8): p. 2091-101. (5) Bartolomei, F. and L. Naccache, The global workspace (GW) theory of consciousness and epilepsy. Behav Neurol, 2011. 24(1): p. 67-74. (6) Blumenfeld, H., Impaired consciousness in epilepsy. Lancet Neurol, 2012. 11(9): p. 814-26. (7) Bartolomei, F., et al., Pre-ictal synchronicity in limbic networks of mesial temporal lobe epilepsy. Epilepsy Res, 2004. 61(1-3): p. 89-104. (8) Selimbeyoglu, A. and J. Parvizi, Electrical stimulation of the human brain: perceptual and behavioral phenomena reported in the old and new literature. Front Hum Neurosci, 2010. 4: p. 46. (9) Isnard, J., et al., Clinical manifestations of insular lobe seizures: a stereoelectroencephalographic study. Epilepsia, 2004. 45(9): p. 1079-90. (10) Penfield, W., Some Mechanisms of Consciousness Discovered during Electrical Stimulation of the Brain. Proc Natl Acad Sci USA, 1958. 44(2): p. 51-66. (11) Kurth, F., et al., A link between the systems: functional differentiation and integration within the human insula revealed by meta-analysis. Brain Struct Funct, 2010. 214(5-6): p. 519-34. (12) Crick, F. C. and C. Koch, What is the function of the claustrum? Philos Trans R Soc Lond B Biol Sci, 2005. 360(1458): p. 1271-9. (13) Lambert, I., et al., Alteration of global workspace during loss of consciousness: a study of parietal seizures. Epilepsia, 2012. 53(12): p. 2104-10. (14) Gabor, A. J. and T. L. Peele, Alterations of Behavior Following Stimulation of the Claustrum of the Cat. Electroencephalogr Clin Neurophysiol, 1964. 17: p. 513-9. (15) Laufs, H., et al., Converging PET and fMRI evidence for a common area involved in human focal epilepsies. Neurology, 2011. 77(9): p. 904-10.

In Laufs et al evidence for a common area involved in human focal epilepsies found evidence that the claustrum and the piriform cortex might be part of the epileptic network in focal epilepsy regardless of the particular localization of the seizure focus. This illustrates the potential of these regions as targets for electrical stimulation for treatment of intractable epilepsy. Other references incorporated herein by reference, include: Electrical Stimulation of a Brain Area Reversibly Interferes with Human Consciousness, which discusses electrode implantation and stimulation of that brain region, and Alteration of consciousness Due to Electrical Stimulation of the Left Anterior Insula/Claustrum Region in the Human Brain to M. Koubeissi et al.; studies in the cat (e.g. 1. Witter M P, Room P, Groenewegen H J, Lohman A H. Reciprocal connections of the insular and piriform claustrum with limbic cortex: an anatomical study in the cat. Neuroscience. 1988/02/01. 1988; 24:519-539, and 2. Gabor A J, Peele T L. Alterations of Behavior Following Stimulation of the Claustrum of the Cat. Electroencephalogr Clin Neurophysiol. 1964/11/01. 1964; 17:513-519.) and hypotheses in humans (e.g. 1. Crick F C, Koch C. What is the function of the claustrum? Philos Trans R Soc Lond B Biol Sci. 2005/09/09. 2005; 360:1271-1279) suggesting a role of the claustrum in consciousness, which the sphere that is commonly altered in seizures.

The description and drawings of the present invention provided in the papers should be considered as illustrative only of the principles of the invention. The invention may be configured in a variety of ways and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. An electrical stimulation device for stimulation of a person's Claustrum and piriform cortex, comprising:
    a stimulator configured to generate a stimulation signal; and
    a first electrode located near the Claustrum and a second electrode adapted to be located near the piriform cortex, said first and second electrodes receiving the stimulation signal from said stimulator and imparting the stimulation signal to the Claustrum and the piriform cortex, wherein the imparted stimulation signal inhibits seizures or prevents seizure propagation.

2. The device of claim 1, wherein said first electrode is located in the Claustrum or within 2 cm of the Claustrum, and said second electrode is located in the piriform cortex or within 2 cm of the piriform cortex.

3. The device of claim 1, further comprising a recording device in electrical communication with said electrode, said recording device receiving electrophysiological signals from said electrode.

4. The device of claim 3, further comprising a signal processing device configured to receive the signals from said recording device, exclude artifacts from the signal, perform analysis, and provide stimulus instruction to said stimulator.

5. The device of claim 1, wherein said first and second electrodes each comprise a deep brain electrode.

6. The device of claim 1, wherein said stimulation signal comprises pulses having bipolar square waves of 0.01 to 5 msec duration.

7. The device of claim 6, wherein said stimulation signal is in the frequency range of 0.01-250 Hz.

8. The device of claim 7, wherein said stimulation signal stimulation signal delivers one or more pulse-trains of various durations, frequencies, and/or current intensities.

9. A stimulation method for stimulation of a person's Claustrum or piriform cortex, comprising:
    generating by a stimulator, a stimulation signal;
    providing a first electrode near the Claustrum;
    providing a second electrode near the piriform cortex;
    receiving the stimulation signal at the electrode; and
    imparting by the first and second electrodes, the stimulation signal to the Claustrum and the piriform cortex, wherein the imparted stimulation signal inhibits seizures or prevents seizure propagation.

10. The method of claim 9, further comprising receiving at a recording device an electrophysiological signal from said first and second electrodes.

11. The method of claim 10, further comprising:
    receiving at a signal processing device the signal from the recording device;
    excluding by the signal processing device, artifacts from the signal;
    perform processing by the signal processing device; and
    providing by the signal processing device, stimulus instruction to said stimulator.

12. The method of claim 9, wherein the first and second electrodes each comprise a deep brain electrode.

13. The method of claim 9, wherein the stimulation signal comprises pulses having bipolar square waves of 0.5 msec duration.

14. The method of claim 13, wherein the stimulation signal is in the frequency range of 0.1-250 Hz.

15. The method of claim 14, wherein the stimulation signal comprises any number of programmed sessions of any number of pulses at frequencies ranging from 0.1-250 Hz at current intensities ranging from 0.01 mA/phase to 10 mA/phase.

16. An electrical stimulation device for stimulation of a person's Claustrum or piriform cortex, comprising:
    a stimulator configured to generate a stimulation signal; and
    a first electrode located in or near the Claustrum and a second electrode located in or near the piriform cortex, said first and second electrodes receiving the stimulation signal from said stimulator and impart the stimulation signal to the Claustrum and the piriform cortex, wherein said imparted stimulation signal inhibits seizures or prevents seizure propagation.

17. An electrical stimulation device, comprising:
    a stimulator configured to generate a stimulation signal;
    a detection electrode located near a seizure onset zone that detects seizure discharges;
    an analyzing device configured to analyze the detected seizure discharges and generate pulses;
    a first stimulator electrode configured to deliver the pulses from said analyzing device to the Claustrum and a second stimulator electrode configured to deliver the pulses from said analyzing device to the piriform cortex, wherein the delivered pulses inhibit seizures or prevent seizure propagation.

18. An electrical stimulation device, comprising:
    a stimulator configured to generate a stimulation signal;
    a first dual function electrode adapted to be located near the Claustrum that detects seizure discharges and delivers pulses to the claustrum, a second dual function electrode adapted to be located near the piriform cortex that detects seizure discharges and delivers pulses to the piriform cortex, wherein the delivered pulses inhibit seizures or prevent seizure propagation;
    a processing device configured to analyze the detected seizure discharges and generate the pulses.

19. The device of claim 18, wherein said stimulator comprises a signal generator.

20. The device of claim 18, wherein said pulses are configured to inhibit seizures or prevent seizure propagation in persons with medically intractable epilepsy, temporal lobe epilepsy, or generalized epilepsy.

21. An electrical stimulation device for stimulation of a person's Claustrum and a brain region apart from the Claustrum, comprising:
    a stimulator configured to generate a stimulation signal; and
    a first electrode adapted to be located in or near the Claustrum and a second electrode adapted to be located in or near the brain region, said first and second electrodes receiving the stimulation signal from said stimulator and impart the stimulation signal to the claustrum Claustrum and brain region, wherein said imparted stimulation signal inhibits seizures or prevents seizure propagation.

22. An electrical stimulation device for stimulation of a person's Claustrum, comprising:

a stimulator configured to generate a stimulation signal; and an electrode adapted to be located in or near the Claustrum, said electrode receiving the stimulation signal from said stimulator and imparting the stimulation signal to the Claustrum, wherein the imparted stimulation signal inhibits seizures or prevents seizure propagation.

* * * * *